(12) United States Patent
McCreath

(10) Patent No.: US 6,740,736 B2
(45) Date of Patent: May 25, 2004

(54) PURIFICATION OF FIBRINOGEN FROM MILK BY USE OF CATION EXCHANGE CHROMATOGRAPHY

(75) Inventor: Graham McCreath, Edinburgh (GB)

(73) Assignee: PPL Therapeutics (Scotland) Limited, Edinburgh (GB)

( * ) Notice: Subject to any disclaimer, the term of this patent is extended or adjusted under 35 U.S.C. 154(b) by 170 days.

(21) Appl. No.: 09/822,299

(22) Filed: Mar. 22, 2001

(65) Prior Publication Data

US 2002/0025932 A1 Feb. 28, 2002

Related U.S. Application Data

(63) Continuation of application No. PCT/GB99/03197, filed on Sep. 24, 1999.
(60) Provisional application No. 60/103,397, filed on Oct. 7, 1998.

(30) Foreign Application Priority Data

Sep. 24, 1998 (GB) ................................. 9820846

(51) Int. Cl.$^7$ .......................... C07K 14/75; C07K 1/18
(52) U.S. Cl. .................. 530/382; 530/380; 530/416; 530/417
(58) Field of Search ............................. 530/382, 380, 530/416, 417

(56) References Cited

U.S. PATENT DOCUMENTS 5,834,420 A    11/1998  Laub et al.

FOREIGN PATENT DOCUMENTS

WO     WO 96/02571     2/1996

OTHER PUBLICATIONS

Gray et al., A–alpha and B–beta chains of fibrinogen stimulate proliferation of human fibroblasts, Journal of Cell Science, (1993) vol. 104, No. 2, pp. 409–413.*
Biological Abstracts, vol. 1993, Philadelphia, PA US; abstract No. 272061, Ajgray et al.; "A–alpha and B–beta chains of fibrinogen stimulate proliferation of human fibroblast" Journals of Cell Science, vol. 104, No. 2, 1993; pp. 409–413, abstract.

* cited by examiner

Primary Examiner—Robert A. Wax
(74) Attorney, Agent, or Firm—Drinker Biddle & Reath LLP

(57) ABSTRACT

Fibrinogen is obtained from milk by contact with a cation exchange chromatography substrate under conditions where the fibrinogen binds to the substrate, followed by optional washing of the substrate. The bound fibrinogen is removed from the substrate by irrigation under increased ionic strength or increased pH conditions. The obtained fibrinogen may be naturally produced or transgenic.

15 Claims, 4 Drawing Sheets

Figure 1. Purification of fibrinogen from solubilised skimmed milk by cation exchange chromatography using a combination of 2 pH elution and 1 salt elution steps.

Figure 2 Purification of fibrinogen from solubilised skimmed milk by cation exchange chromatography using a combination of 1 pH elution and 1 salt elution step.

Figure 3. Purification of fibrinogen from skimmed milk and solubilised skimmed milk using a combination of 1 pH elution and 1 salt elution step.

PURIFICATION OF FIBRINOGEN FROM MILK BY USE OF CATION EXCHANGE CHROMATOGRAPHY

This is a continuation of co-pending international application PCT/GB99/03197, published in English, having an international filing date of Sep. 24, 1999, which claims the benefit under 35 U.S.C. 119(e) of the filing date of provisional application Serial No. 60/103,397, filed Oct. 7, 1998, abandoned.

This invention is concerned generally with protein purification and specifically with the purification of fibrinogen from the milk of transgenic animals using cation exchange chromatography.

Fibrinogen, the main structural protein in the blood responsible for the formation of clots exists as a dimer of three polypeptide chains; the Aα (66.5 kD), Bβ (52 kD) and γ (46.5 kD) are linked through 29 disulphide bonds. The addition of asparagine-linked carbohydrates to the Bβ and γ chains results in a molecule with a molecular weight of 340 kD. Fibrinogen has a trinodal structure, a central nodule, termed the E domain, contains the amino-termini of all 6 chains including the fibrinopeptides (Fp) while the two distal nodules termed D domains contain the Carboxy-termini of the Aα, Bβ and γ chains. Fibrinogen is proteolytically cleaved at the amino terminus of the Aα and Bβ chains releasing fibrinopeptides A and B (FpA & FpB) and converted to fibrin monomer by thrombin, a serine protease that is converted from its inactive form by Factor Xa. The resultant fibrin monomers non-covalently assemble into protofibrils by DE contacts on neighboring fibrin molecules. This imposes a half staggered overlap mode of building the fibrin polymer chain. Contacts are also established lengthwise between adjacent D domains (DD contacts) leading to lateral aggregation. Another serine protease, Factor XIII is proteolytically cleaved by thrombin in the presence of $Ca^{2+}$ into an activated form. This activated Factor XIII (Factor XIIIa) catalyses crosslinking of the polymerised fibrin by creating isopeptide bonds between lysine and glutamine side chains. The first glutamyl-lysyl bonds to form are on the C-terminal of the γ chains producing D—D crosslinks. Subsequently, multiple crosslinks form between adjacent Aα chains, the process of crosslinking imparts on the clot both biological stability (resistance to fibrinolysis) and mechanical stability [Sienbenlist and Mosesson, Progressive Cross-Linking of Fibrin y chains Increases Resistance to Fibrinolysis, *Journal of Biological Chemistry*, 269: 28414–2841, 1994].

The coagulation process can readily be engineered into a self sustained adhesive system by having the fibrinogen and Factor XIII as one component and thrombin and $Ca^{2+}$ as the second component which catalysis the polymerization process. These adhesion systems, know in the art as "Fibrin Sealants" or "Fibrin Tissue Adhesives" have found numerous application in surgical procedures and as delivery devices for a range of pharmaceutically active compounds [Sierra, Fibrin Sealent Adhesive Systems: A Review of Their Chemistry, Material Properties and Clinical Applications, *Journal of Biomaterials Applications*, 7:309–352, 1993; Martinowitz and Spotnitz, Fibrin Tissue Adhesives, *Thrombosis and Haemostasis*, 78:661–666, 1997; Radosevich et al., Fibrin Sealent:Scientific Rationale, Production Methods, Properties and Current Clinical Use, *Vox Sanguinis*, 72:133–143, 1997].

It has been estimated that the annual US clinical need for fibrin sealants is greatly in excess of the 300 kg/year that can be harvested using the current cryoprecipitation methods used by plasma fractionaters. Alternative sources of fibrinogen, by far the major component in fibrin sealant, have therefore been explored with recombinant sources being favored [Butler et al., Current Progress in the Production of Recombinant Human Fibrinogen in the Milk of Transgenic animals, *Thrombosis and Haemostasis*, 78: 537–542, 1997]. While cell culture systems have demonstrated the ability to produce small amounts (1–4 ug/ml) of fibrinogen, it has been shown that mammals are capable of producing transgenic human fibrinogen at levels of up to 5.0 g/L in their milk making this a commercially viable method for the production of human fibrinogen [Prunkard et al., High-level expression of recombinant human fibrinogen in the milk of transgenic mice, *Nature Biotechnology*, 14:867–871, 1996; Cottingham et al., Human fibrinogen from the milk of transgenic sheep. In: *Tissue Sealants: Current Practice, Future Uses*. Cambridge Institute, Newton Upper Falls, Mass., Mar. 30-Apr. 2, 1996 (abstract)].

Differences have been identified between recombinant human fibrinogen and fibrinogen which has been purified from human plasma. Fibrinogen which has been purified from human plasma has two alternately spliced gamma chains (γ and γ'). In contrast, recombinant human fibrinogen only has the major form γ. Further, the glycosylation of the beta and gamma chains (there is no N-linked glycosylation of the alpha chain) of recombinant human fibrinogen differs slightly from that on plasma derived fibrinogen, but is similar to the glycosylation found on other proteins expressed in the milk of transgenic animals. In addition, the Ser3 of the alpha chain of recombinant human fibrinogen is more highly phosphorylated than Ser3 of the alpha chain of plasma derived fibrinogen, although the difference in phosphorylation does not result in functional differences. Also, there are detectable differences in heterogeneity caused by C-terminal proteolysis of a number of highly protease-sensitive sites on the alpha chain. Differences of a similar magnitude are also observed between plasma-derived fibrinogen from different sources.

Another driving force for the development of totally recombinant fibrin-based sealants stems from the fact that commercially available adhesives originate from pooled plasma. As blood-derived products have been associated with the transmission of human immunodefieciency virus (HIV), hepatitis virus and other etiological agents, the acceptance and availability of such adhesives is limited. While the incorporation of viral removal and inactivation procedures has increased the safety of these products (for example, U.S. Pat. Nos. 4,960,757 and 5,116,950), plasma derived fibrinogen is still not without risk. The use of autologous plasma reduces the risk of disease transmission; however, autologous adhesives can only be used in elective surgery when the patient is able to donate the blood in advance.

While the main use of fibrinogen is thought to be for the preparation of adhesive or sealing agents, fibrinogen also has other applications in the field of medicine, for example as a coating for polymeric articles as disclosed in U.S. Pat. No. 5,272,074, and the concern for safety apply to any of these other uses in medicine.

Various methods for the purification of fibrinogen have been described where, in most cases, the starting material has been either plasma or more usually cryoprecipitate or Cohn Fraction 1, both of which are rich in fibrinogen. Schwartz et al., [U.S. Pat. Nos. 4,362,567; 4,377,572; 4,414, 976] have disclosed a process for the manufacture of fibrinogen tissue adhesive using cryoprecipitation of plasma as the major purification step. Burnouf et al., (1990) [Biochemical and Physical Properties of a Solvent-Detergent-Treated Fibrin Glue, *Vox Sang* 58:77–84] describe a process for the preparation of fibrinogen concentrate from 150 L of human plasma. After thawing anticoagulated plasma at 37° C., the plasma was subjected to a 10% ethanol precipitation. Following dissolution of the precipitated fibrinogen a Solvent-Detergent viral inactivation technique was used followed by a further two ethanol precipitation procedures to remove the Solvent-Detergent chemicals. The final material is quoted as being 93.5% pure with respect to protein content and is sold under the trade name Biocoll©.

Vila et al., (1985) [A Rapid Method for Isolation of Fibrinogen From Human Plasma by Precipitation with PEG 6000, *Thrombosis Research* 39:651–656] describe a method whereby fibrinogen is precipitated from citrated plasma using an 8% solution of PEG 6000. Following dissolution the fibrinogen is then further precipitated using 2 mol/l acetic acid-acetate buffer pH 4.6. A final precipitation with ammonium sulphate is used to give a product with 93±6% clottable protein and in 60±9% yield. Using similar techniques, Masri et al., (1983) [Isolation of Human Fibrinogen of High Purity and in High Yield using PEG 1000, *Thrombosis and Haemostasis,* 49:116–119] have also purified fibrinogen from thrombin-free plasma using precipitation with PEG 1000. A three stage precipitation technique was used leading to a product with 98% clottable protein in 65–70% yield.

It is evident from the literature that the purification of fibrinogen from plasma is usually accomplished using precipitation techniques. In many examples this leads to relatively pure product but it is doubtful that a process based solely on precipitation could be used in the purification of human fibrinogen from milk. Fibrinogen has a propensity for binding other plasma proteins including but not exclusively plasminogen, tPA, factor XIII and fibronectin which are often co-purified during precipitation techniques. Numerical data of some of these proteins are often quoted in manufacturers specifications. This contamination can be tolerated in human plasma-derived fibrinogen, which is destined to be used in humans, as the contaminating human proteins would probably not be antigenic in humans. However, it is unacceptable for high levels of these proteins to be present in a human fibrinogen product manufactured from non-human animal milk, as these proteins, from the milk of a different species, would probably be expected to be antigenic in humans. Hence it is anticipated that any purification scheme from milk would include several chromatographic techniques.

The purification of fibrinogen from human plasma using column chromatography has been described by Dempfle and Keen (1987) [Purification of Human Plasma Fibrinogen by Chromatography On Protamine Agarose, *Thrombosis and Haemostasis* 46:19–27]. Fibrinogen was recovered in a single-step operation in 65–80% yield with >90% clottability. The use of Protamine agarose is well known in the art and has been used extensively at a small scale for purification of fibrinogen from plasma and from recombinant sources including mammalian cell culture [Lord et al., Purification and characterization of recombinant human fibrinogen, *Blood Coagulation and Fibrinolysis* 4:55–59, 1993] and yeast [Roy et al., Secretion of Biologically Active Recombinant Fibrinogen by Yeast, *Journal of Biological Chemistry,* 270:23761–23767, 1995). However, even though the technique is very specific, the expense of the chromatography media and the suspected lability of the biological ligand render it nonviable on a commercial large-scale. Other examples of very specific chromatographic steps are available in the literature including the use of peptide ligands [Kuyas et al., Isolation of Human Fibrinogen and its Derivatives by Affinity Chromatography on GlyProArgProLys-Fractogel, *Thrombosis and Haemostasis,* 63:439–444, 1990] and even the use of columns containing monoclonal antibodies [Takebe et al., Calcium Ion Dependent Monoclonal Antibody Against Human Fibrinogen: Preparation, Characterization and Application to Fibrinogen Purification, *Thrombosis and Haemostasis,* 73:662–667, 1995]. However as discussed above, the use of such expensive and delicate chromatographic materials remains cost-prohibitive at an industrially enabling scale.

As an alternative to the use of biological ligands, anion exchange chromatography has been practiced during the purification of fibrinogen from plasma, although this has been done mostly at an analytical scale where its incorporation is to subfractionate fibrinogen species [Kuyas et al., A Subfraction of Human Fibrinogen With High Sialic Acid Content and Elongated γ Chains, *Journal of Biological Chemistry,* 257:1107–1109, 1982]. An anion exchange purification technique for fibrinogen has been disclosed by Bernard et al. (EP 0 555 135 A1), in which fibrinogen is bound from treated cryoprecipitate in 120 mM NaCl, 10 mM Tris, pH 8.8 and eluted at 200 mM NaCl, 10 mM Tris, pH 8.8. This procedure leads to greater selectivity in terms of the eluted fibrinogen.

In developing a purification process from transgenic milk it is generally accepted that eliminating casein is a high priority (Wilkins & Velander, "Isolation of Recombinant Proteins from Milk", *Journal of Cellular Biochemistry* 49:333–338 [1992]). Casein is a mixture of mostly insoluble proteins present as micellar suspensions (the remainder of proteins in milk are called whey proteins). Casein micelles are not filterable and readily block process equipment. This property prevents milk from being processed by conventional chromatography columns before casein removal or solubilisation. This has inspired the recent development of techniques for casein removal or solubilisation. For example Denman ["Isolation of Components of Interest From Milk", PCT WO 94/19935] has disclosed a method for solubilising casein micelles by the addition of positively charged agents. This results in making the milk more amenable for processing. However, this technique does not remove casein, and the agents used are prohibitively expensive for large scale processing. Kutzko et al. ["Purification of Biologically Active Peptides From Milk", PCT WO 97/42835] have disclosed a method for the separation of a soluble milk component from milk using tangential flow filtration. This technique involves adding a chelating agent to the milk to solubilise casein before applying to ultrafiltration apparatus whereby the component of interest is collected in the permeate and the solubilised casein remains in the retentate. This technique has also been useful with milk in which the casein fraction has not been solubilised. However, it is expected that this technique is more suited to peptides and small proteins. Furthermore, this technique although useful in providing a casein-free solution, does not offer significant purification of the transgenic protein unless it is linked with another unit operation, for example, chromatography. Therefore it is apparent that while milk can be more amenable to processing using the techniques described above, a process comprising simultaneous casein removal and fibrinogen purification would have significant economic advantages.

On a small scale, elimination of casein can be achieved by centrifugation; however, as the centrifugation force needs to be very high this is not a viable technique for industrial application. Historically, casein removal in the food industry has been carried out either by the addition of rennet or by the use of acid; both of which result in casein precipitation [Swaisgood, *Developments in Dairy Chemistry—1: Chemistry of Milk Protein,* Applied Science Publishers, N.Y., 1982]. Again these are not generally applicable or preferred techniques for the purification of human proteins from milk e.g. renin is animal derived and would have to be obtained from a controlled source that is pathogen free. Precipitation by acid, while being cost-effective and efficient, is not generally applicable, as the low pH may result in degradation or precipitation of the human protein unless the human protein is acid stable.

Precipitation of caseins with low concentrations of salts and polymeric precipitating agents has been described in the literature. For example approximately 17% sodium sulphate and 22% ammonium sulphate have been used to precipitate casein micelles before further fractionation of whey proteins [Swaisgood, *Developments in Dairy Chemistry*—1: *Chemistry of Milk Protein*, Applied Science Publishers, NY, 1982]. Lee and Antonsen [PCT WO 97/09350] have disclosed that precipitation of casein with PEG is used as an early step in the purification of transgenic alpha-1-antitrypsin from sheep milk. Similarly, Wilkins & Velander, (1992) [Isolation of Recombinant Proteins from Milk, *Journal of Cellular Biochemistry* 49:333–338] advocate the use of PEG precipitation of casein as an early step in transgenic protein purification.

With respect to the purification of fibrinogen from milk, a major obstacle is the separation of the casein fraction. Fibrinogen and casein micelles share several characteristics, most notably their relatively insoluble nature and propensity for self-aggregation. They can also both be regarded as relatively hydrophobic with a tendency to bind non-specifically to both other proteins and surfaces. The similar properties shared between casein and fibrinogen is also illustrated by the fact that both are readily purified by precipitation. From the evidence in the literature therefore, it would be unlikely that precipitation could be solely employed as a stand alone technique for the removal of fibrinogen from casein. Consequently, a method for fibrinogen purification from milk which combined both casein removal and fibrinogen purification would be a significant advantage.

Thus there remains a need in the art for a method of obtaining purified fibrinogen from milk (which transgenic origin gives the fibrinogen the advantages of significant yields and safety in terms of viral non-contamination), the method in its preferred embodiment providing highly purified, non-antigenic fibrinogen in a simple, cost-effective and efficient manner. A major obstacle is the separation of fibrinogen from casein, which is difficult due to certain similarities in their properties.

Cation ion exchange chromatography (CEX) is a separation technique which exploits the interaction between positively charged groups on a protein and negatively charged groups on a substrate. As pH influences charges on proteins, the pH of the medium in which CEX is carried out greatly influences the separation performance. CEX substrates can be grouped into 2 major types; those which maintain a negative charge on the substrate over a wide pH range (strong CEX substrates) and those which maintain a negative charge on the substrate over a narrow pH range (weak CEX). Strong cation exchange substrates usually incorporate sulphonic acids derivatives as functional groups (e.g. Sulphonates, S-type or Sulphopropyl groups, SP-types). In order to maximize the performance of the CEX substrate, in terms of binding, the pH of the medium in which the separation is carried out is usually below the isoelectric point of the protein to be bound (the isoelectric point or pI of a protein is that pH value at which the protein carries no net charge, at pH values above the pI, the protein has a net negative charge and at pH values below the pI, the protein has a net positive charge and will be bound to a CEX substrate). CEX has been used quite extensively in the separation of milk proteins particularly the casein fraction. For example, Law et al., [Quantitative Fractionation of Ovine Casein by Cation-Exchange FPLC, *Milchwissenchaft*, 45: 279–282, 1992] have described the resolution of casein into subfamilies using a Mono S™ column at pH 5.0. Similarly, Leaver and Law [Preparative-scale Purification of Bovine Caseins on a Cation Exchange Resin, *Journal of Dairy Research*, 59: 557–561, 1992] have described the separation of bovine casein from acid precipitated whole casein on S-Sepharose Fast Flow™ at pH 5.0. Whey proteins have also been separated by CEX chromatography. For example, Hahn et al., [Bovine Whey Fractionation based on Cation-Exchange Chromatography, *Journal of Chromatography A*, 795: 277–287, 1997] describe the separation of the major whey proteins at pH 4.6 using milk which was acidified to remove the casein fraction. This method, however, is inappropriate for the purification of fibrinogen from milk, as the casein removal by acidification would precipitate fibrinogen.

The isolation of lactoferrin from milk using CEX is disclosed in WO 95/22258 (Gene Pharming Europe BV). However, the teaching of WO 95/22258 would not be considered applicable for the purification of fibrinogen due to the differences in the properties of lactoferrin and fibrinogen, and moreover, the elevated ionic strength conditions under which the milk is contacted with the CEX resin in WO 95/22258 would result in fibrinogen not binding to the CEX resin.

The use of CEX in the purification of fibrinogen has not been considered appropriate as fibrinogen is reported to have a pI of 5.5 and can therefore be described as an acidic protein more suited to anion exchange chromatography [Marguerie et al., The Binding of Calcium to Bovine Fibrinogen, *Biochimica et Biophysica Acta*, 490: 94–103, 1977; Weisel and Cederholm-Williams, Fibrinogen and Fibrin: Characterization, Processing and Applications, *Handbook of Biodegradable Polymers* (Series: Drug Targetting and Delivery) 7:347–365, 1997]. The problem of casein removal for an acidic protein was highlighted by Van Cott et al (Affinity Purification of Biologically Active and Inactive Forms of Recombinant Human Protein C Produced in Porcine Mammary Gland, *Journal of Molecular Recognition*, 9: 4407–414 [1996]) who describe previous significant losses of acidic protein C if conventional centrifugation or precipitation steps are used to remove the casein fraction. Solubilisation of casein micelles using EDTA followed by anion exchange chromatography still resulted in casein contamination of human protein C. Up to 20% contamination of protein C by casein following, even highly selective immunoaffinity chromatography, was evidnent if high salt concentrations were not used prior to the immunoaffinity chromatography step. The consequences of using high salt in this step were that up to 20% of the protein C did not bind to the immunoaffinity column.

Of some surprise therefore to the inventors was the fact that fibrinogen can be bound to CEX substrates at pH values above the reported pI of the protein directly from milk and that this attribute can be used to develop a very effective purification technique. The majority of milk proteins, including casein, being relatively acidic in nature, can be prevented from binding to the CEX column or can be resolved from the fibrinogen by the use of changes in pH or ionic strength. Such a finding constitutes a part of this invention. A further advantage of this technique is that prior removal of the casein fraction, by the use of precipitation techniques favored by practitioners, is not necessary. This advantage is thought to provide a significant economic incentive to the incorporation of CEX in a purification protocol for the manufacture of fibrinogen from transgenic non-human sources.

SUMMARY OF THE INVENTION

This patent application describes techniques whereby Cation Exchange Chromatography is used in the purification of transgenic fibrinogen from milk. The techniques can be applied to whole milk, skimmed milk or a milk fraction using a variety of chromatography contacting modes. As the prior removal of casein is not required, the use of precipitation agents and centrifigation equipment can be avoided and therefore process economics can be improved. Fibrinogen may be collected at a high yield (up to 95%) in a very pure state (up to 90%) with very little casein contamination and so the step may be considered as incorporating casein removal and substantial fibrinogen purification into a single unit operation. The fibrinogen requires no further purification or only subsequent minor purification using conventional protein purification techniques.

This invention is based on the finding that cation exchange chromatography can be employed, at a pH value higher than the reported pI of fibrinogen, in the purification of fibrinogen from milk. The present application describes, inter alia, a process wherein cation exchange chromatography is employed at a pH value higher than the reported pI of fibrinogen in the purification of fibrinogen from milk, thus allowing for the substantial purification of fibrinogen while simultaneously removing the casein fraction. In the present invention, the need for expensive filtration equipment as outlined by Kutzko (WO 97/42835) is not necessary for the removal of insoluble milk components. Before cation exchange chromatography, the milk is simply delipidated using commercial continuous flow centrifuges which are ubiquitous in the milk processing industry. As such, the cation exchange chromatography purification procedure integrates casein removal and substantial fibrinogen purification into a single unit operation and this is believed to provide a significant economic incentive to adoption of this technique. More specifically, milk, which may contain a chelating agent or other agent capable of disrupting casein micelle structure, is contacted with a CEX substrate under conditions of pH which favour adsorption of fibrinogen but discourage binding of milk proteins. The substrate is then washed and eluted with a series of buffers of suitable pH and/or ionic strength resulting in the resolution of fibrinogen from milk proteins in a substantially purified form. The technique can be applied to whole milk, skimmed milk or a milk fraction.

DETAILED DESCRIPTION OF THE INVENTION

Figure 1:
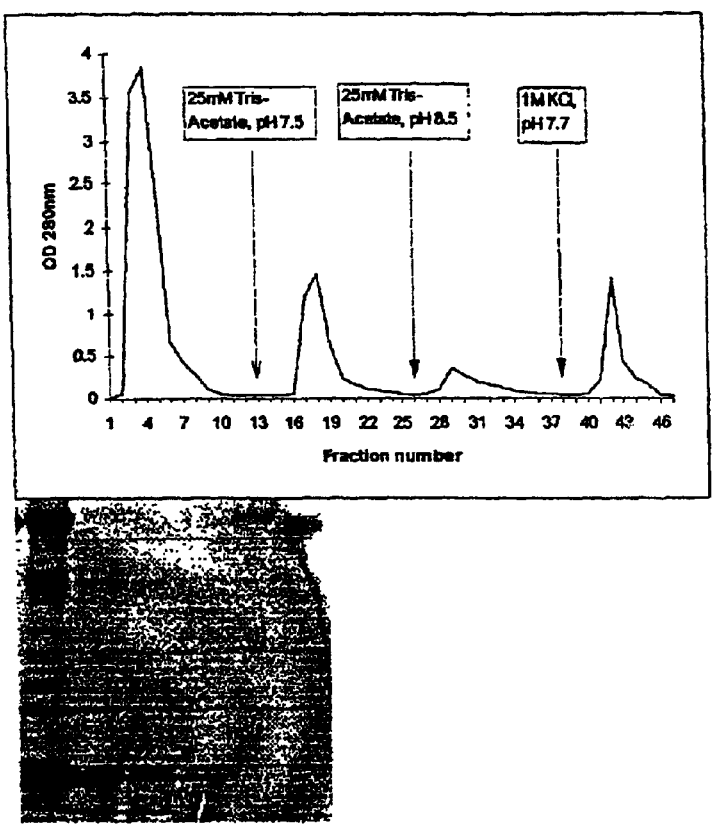
FIG. 1 shows a chromatogram and electrophorogram demonstrating the selectivity of CEX for fibrinogen and the purity of the eluted product.
Figure 2:
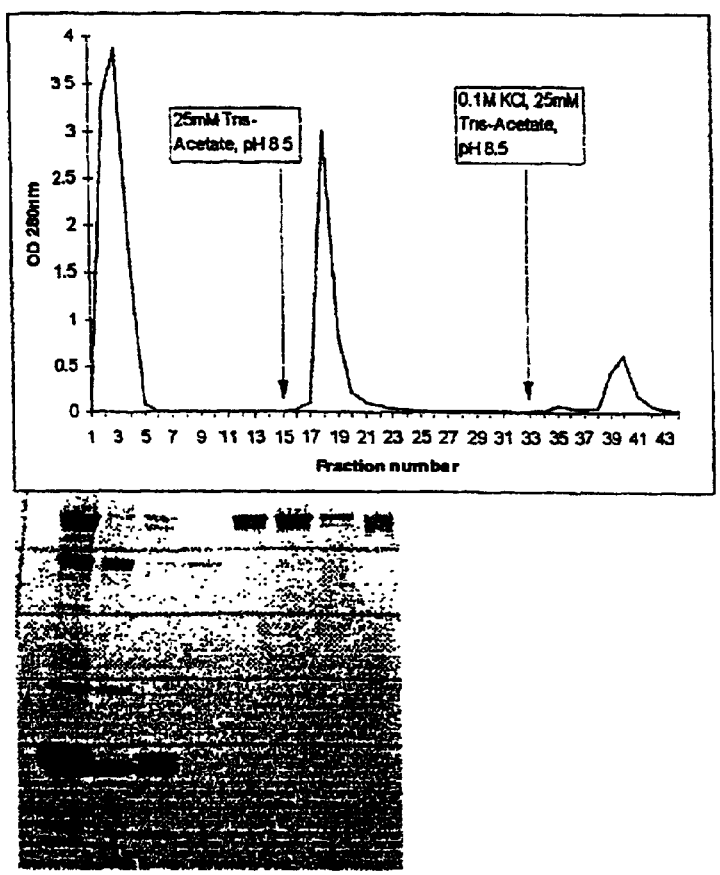
FIG. 2 shows a chromatogram and electrophorogram demonstrating that combinations of pH and ionic strength can be used in the production of very pure fibrinogen from milk using CEX.

The invention provides a method whereby fibrinogen can be significantly purified from milk using cation exchange chromatography at a pH of greater than 5.5 but less than 8.0. The pH is chosen to provide a means for binding the fibrinogen to a CEX substrate which may be of the strong or weak type as described above. It is believed, although the invention should not be read as limiting to this theory, that the driving force for fibrinogen binding to the CEX substrate may be the Aα chains which are known to be more basic than either the Bβ chains or γ chains [Weinstein and Deykin, 1978, Low Solubility Examined by Two-Dimensional Sodium Dodecyl Sulfate Gel Electrophoresis and Isoelectric Focussing, *Thrombosis Research,* 13:361–377] and may therefore allow the fibrinogen to bind at a pH value higher than the reported pI value.

Accordingly, in the first aspect, the present invention provides a method for obtaining fibrinogen from milk, comprising:
(a) contacting the milk with a cation exchange chromatography substrate under conditions where the fibrinogen binds to the substrate;
(b) optionally washing the substrate to remove unbound components; and
(c) removing the bound fibrinogen from the substrate by using irrigating means, which irrigating means has an increased ionic strength or increased pH or both relative to the conditions in step (a).

As used herein, the term "fibrinogen" refers to the main structural protein responsible for the formation of clots and includes the whole glycoprotein form of fibrinogen, as well as other related fibrinogen species including truncated fibrinogen, amino acid sequence variants (muteins or polymorphic variants) of fibrinogen, a fibrinogen species which comprises additional residues, and any naturally occurring allelic variants of fibrinogen.

As used herein, "milk" is to understood to be the fluid secreted from the mammary gland in animals and includes whole milk, skimmed milk and any fractions of milk. Before cation exchange chromatography, the milk may be delipidated using commercial continuous flow centrifuges which are ubiquitous in the milk processing industry. The milk may be obtained from any lactating animal, but especially those which produce milk in quantities, such as cows, sheep, goats, rabbits or even camels or pigs.

The fibrinogen may be naturally present in milk. However, it will more probably be from transgenic sources, i.e. as a result of genetic manipulation of a milk-producing animal such as a sheep or a cow, such that a nucleic acid material encoding fibrinogen is expressed in the mammary gland of the animal and fibrinogen is secreted in the milk. The present invention is useful for the purification of fibrinogen per se or fibrinogen which has been altered in some way to facilitate transgenic expression and/or its isolation, such as by fusion to other proteins. The fibrinogen may be human fibrinogen or fibrinogen from any other suitable animal, such as a sheep or a cow. For medical uses, it is preferred to employ proteins native to the patient. Where the fibrinogen is recombinantly encoded, so that fibrinogen is from a species other than the species in which the fibrinogen is being expressed, the glycosylation pattern may be different from the glycosylation patterns of naturally occurring fibrinogen. Thus, human fibrinogen expressed in a transgenic non-human animal may have a different glycosylation pattern from naturally occurring human fibrinogen. The present invention is useful for purifying any such transgenic fibrinogen.

As used herein, cation exchange chromatography (CEX) substrates are chromatography resins which contain negatively charged groups. Proteins are separated on the basis of the interaction between negatively charged groups in the resin and positively charged groups on a protein. As described above, they can be grouped into two major types; those which maintain a negative charge on the resin over a wide pH range (strong CEX substrates) and those which maintain a negative charge on the resin over a narrow pH range (weak CEX substrates). Strong cation exchange resins usually incorporate sulphonic acids derivatives as functional groups (e.g. Sulphonates, S-type or Sulphopropyl groups, SP-types). Both types of substrates are covered.

Examples of suitable strong CEX substrates include S-Sepharose FF, SP-Sepharose FF, SP-Sepharose Big Beads (all Amersham Pharmacia Biotechnology) and Fractogel EMD-$SO_3$ 650 (M) (E. Merck, Germany). Examples of weak cation exchange substrates include CM Sepharose FF (Amersharn Pharmacia Biotechnology).

The condition in step (a) under which fibrinogen in milk binds to the substrate is where the substrate and the milk is at a pH which is higher than the pI value of fibrinogen.

The pI, or the isoelectric point, of a protein is that pH value at which the protein carries no net charge. At pH values above the pI, the protein has a net negative charge and at pH values below the pI, the protein has a net positive charge. As used herein, the pI of fibrinogen is to be understood to be pH 5.5 according to reported sources [Marguerie et al., The Binding of Calcium to Bovine Fibrinogen, *Biochimica et Biophysica Acta,* 490: 94–103, 1977; Weisel and Cederholm-Williams, Fibrinogen and Fibrin: Characterization, Processing and Applications, *Handbook of Biodegradable Polymers* (Series: Drug Targetting and Delivery), 7:347–365, 1997].

Preferably, the condition in step (a) is such that the substrate and the milk is at pH which is greater than 5.5. More preferably, the pH is around 6.0.

Once fibrinogen has bound to the substrate, the substrate is preferably washed by an irrigating means of suitable pH and ionic strength to remove the majority of non-fibrinogen components. A suitable irrigating means would be a buffer of pH 6.0 or of a higher pH, such as a buffer with a pH greater than 5.5 but less than 14.0, preferably between pH 6.0–8.5. An example is Tris-acetate buffer at a pH of 6.0–8.5 containing 0–0.2M sodium or potassium chloride. Generally, the concentration of sodium or potassium chloride (or any other salt useful in increasing solution conductivity and ionic strength) required to remove non-fibrinogen components from the substrate while retaining bound fibrinogen is dependent on the pH at which it is applied. Therefore it is found that if low pH (5.5–6.5) is used, the concentration of salt required is in the range 0–0.15M. If the pH of the salt solution is increased, for example to greater than 6.5, (this has the effect of weakening the strength of interaction between bound fibrinogen and CEX substrate) the concentration of salt required is generally in the range 0–0.1M. This invention should not however be taken to be limited with respect to the conditions given above as those familiar with the art may establish conditions different to the above to achieve the same results.

Fibrinogen can then be eluted from the column by increasing either the ionic strength or pH or both of the irrigating means relative to the irrigating means in step (b) (or relative to the conditions in step (a) if there was no step (b)). A suitable irrigating means is a buffer with a pH greater than 5.5 but less than 9.0, preferably between pH 6.0–8.5; and with an ionic strength of between 0–1.0M, preferably 0.025–0.2M. The irrigating means in step (c) has an ionic strength of equal to or greater than 0.1M if the pH of it were 5.5–6.5. Similarly, if the irrigating means in step (c) had a pH of 6.5–8.5, the ionic strength of the irrigating means would generally be greater than or equal to 0.05M. It may be desirable for the ionic strength of the eluted product in step (c) to be less than 0.2M if the fibrinogen were to be further processed using another ion exchange step. This invention should not however be taken to be limited with respect to the conditions given above as those familiar with the art may establish conditions different to the above to achieve the same results. The invention is appropriate for small, medium and large scale practice.

The fibrinogen obtained according to the method is separated or isolated and is at least 60%, preferably 80%, most preferably 90% free from other components. The recovery rates of fibrinogen in milk with this method of invention are at least about 65%, preferably 85%, more preferably 90%, most preferably 95% of the total fibrinogen in the milk. Preferably, the recovery rates are in the range of about 65% to about 90%, more preferably in the range of about 65% to 95%. The fibrinogen can then be further purified using techniques well known to those in the art, for example using anion exchange chromatography as described by Kuyas et al. [A subfraction of human fibrinogen with high sialic acid content and elongated γ chains, *Journal of Biological Chemistry* 257 1107–1109 (1982) and Bernard et al (EP 0 555 135 A1).

The milk may contain one or more agents capable of disrupting casein micelles. Casein micelles are micelle structures formed in milk by a mixture of mostly insoluble proteins, which are not filterable and readily block process equipment. Examples of such agents include chelating agents such as EDTA and EGTA at a concentration of 20–100 mM or citrate at a concentration of 50–200 mM. Other agents such as the ones disclosed in Denmen, WO 94/19955 and Denman, U.S. Pat. No. 5,756,687 may also be used if desired, although using these agents may increase the solution ionic strength to a point which prevents or reduces fibrinogen binding, and also the cost may be prohibitive on a commercial scale.

The method may be performed with the substrate in a batch format or a column format. In batch format, the milk or milk fraction may be contacted with the CEX substrate in a well stirred tank. Separation of the CEX substrate from the milk may then be facilitated by sedimentation or be centrifugally assisted. In column format, which is preferred, the milk or milk fraction would be pumped through a column into which CEX substrate had already been added. Column formats are preferred as they result in greater adsorption efficiency. This column format could be regarded as either a "Packed" or "Fixed" bed format. If casein solubilisation is not carried out, batch techniques may be preferable although column chromatography may be carried out using traditional "Packed bed contactors" providing that the substrate bead size is of a sufficient size not to be clogged or otherwise blocked with casein. It is envisioned that the use of "Expanded bed" or "Fluidised bed" contactors may also be applicable(Noppe et al, Simple Two-Step Procedure for the Preparation of Highly Active Pure Equine Lysozyme, *Journal of Chromatography A*719 327–331 (1996) and Hjorth, Expanded-Bed Adsorption in Industrial Bioprocessing: Recent Developments, *Trends in Biotechnology* 15 230–235 (1997)).

Expanded and Fluidised bed contactors can be regarded as having characteristics of both batch adsorption techniques and Packed (Fixed) bed contactors. As illustrated in the above references, they allow for the processing of solid containing or particulate feedstocks. This is achieved by virtue of the fact that the feedstock is applied to a column containing adsorbent substrate (normally in beaded form) from the bottom of the column while the top of the column is unconstrained and the resin beads allowed to move in an upward direction. Parameters such as flow rate and feedstock viscosity and density then control the degree of bed expansion, that is, suspension of the beaded substrate. As the beaded substrate becomes suspended in the column, the spaces between the beads increase (the bed voidage increases) such that particles and suspended solids are allowed to pass through the bed unhindered. This is in contrast to applying particulate containing feedstocks to a conventional Packed or Fixed Bed column whereby the substrate beads would act as a filter for the particles and eventually become blocked; blockage manifests itself by an increase in pressure drop across the column and a decrease in the flow rate of liquid through the column. The terms Expanded and Fluidised are often interchanged. In Chemical Engineering terms, Fluidised Beds would represent a bed of substrate beads which exhibited a greater degree of backmixing than would be shown by an Expanded Bed. In certain circumstances, for example, when the feedstock had a small concentration of particles the use of Expanded or Fluidised Beds may not be necessary. If the substrate beads are of sufficiently large size (>100 um), the spaces between the beads are large enough to allow the passage of small particles. An example of such a substrate would be Sepharose Big Beads (Amersham Pharmacia Biotechnology) which is available with a range of ion exchange groups.

In the second aspect of the present invention, the use of cation exchange chromatography for obtaining fibrinogen from milk is provided.

The preferences described for the first aspect of the invention apply to the second aspect of the invention.

In the third aspect of the present invention, there is provided fibrinogen which is substantially free from viral contamination. Fibrinogen obtainable according to the method as set out in the first aspect of the invention is also provided.

Preferred features of the first aspect of the invention also apply to the third aspect.

In the fourth aspect, the present invention provides a fibrin adhesive or sealent containing fibrinogen which is as set out in the first aspect of the invention.

As used herein the term "fibrin adhesive or sealent" describes a substance containing fibrinogen which is capable of forming a biodegradable adhesive or seal by the formation of polymerised fibrin. Such adhesive/sealent systems are alternatively called "fibrin tissue adhesives". The adhesive or seal may act as, inter alia, a hemostatic agent, a barrier to fluid or air, a space-filling matrix or a drug-delivery agent. Particular use may be found in neurosurgery, opthalmic, orthopedic or cardiothoracic surgery, skin grafting, and various other types of surgeries.

Other than fibrinogen, the fibrin adhesive or sealent may contain substances which encourage the formation of the fibrin adhesive/seal, such as thrombin, $Ca^{2+}$ and Factor XIII. As used herein, the term "Factor XIII" includes the active form of Factor XIII, which is Factor XIIIa. Whilst thrombin would be the preferred enzyme to incorporate into any system whereby the formation of a fibrin clot is desired, there are other enzymes capable of proteolytically cleaving fibrinogen resulting in the formation of a fibrin clot. An example of this is the snake venom enzyme Batroxobin (Weisel and Cederholm-Williams, loc. cit.) Other compounds such as albumin, fibronectin, solubilisers, bulking agents and/or suitable carriers or diluents may also be included if desired.

One advantage of fibrin sealent as a biodegradable polymer is that there are natural mechanisms in the body for the efficient removal of clots and thus the fibrin sealent may be a temporary plug for hemostasis or wound healing. Various proteolytic enzymes and cells can dissolve fibrin depending on the circumstances, but the most specific mechanism involves the fibrinolytic system. The dissolution of fibrin clots under physiological conditions involves the binding of circulating plasminogen to fibrin, and the activation of plasminogen to the active protease, plasmin, by plasminogen activators which may also be bound to fibrin. Plasmin then cleaves fibrin at specific sites.

Depending on the situation, it may be advantageous to let the natural process of fibrin breakdown take place after applying a fibrin adhesive or sealent to a site. Indeed, this breakdown may be encouraged, for example, by the inclusion of plasminogen. Alternatively, in some situations it may be advantageous to delay the process by including antifibrinolytic compounds which can, for example, block the conversion of plasminogen to plasmin or directly bind to the active site of plasmin to inhibit fibrinolysis. Such antifibrinolytics include $\alpha_2$-macroglobulin, which is a primary physiological inhibitor of plasmin; aprotinin; $\alpha_2$-antiplasmin; and $\epsilon$-amino caproic acid.

The fibrin adhesive/sealent may comprise two components, one component containing fibrinogen and Factor XIII and the other component containing thrombin and $Ca^{2+}$. Other substances as described above may be included in one or both of the components if desired.

Preferred features of the first aspect of the invention also apply to the fourth aspect.

In the fifth aspect, the present invention also provides a kit comprising fibrinogen as set out in the third aspect of the invention and instructions for use. The kit may also comprise thrombin and the components may be used separately, simultaneously or sequentially.

The kit may further comprise $Ca^{2+}$ and Factor XIII.

The fibrinogen may be provided in any suitable or convenient state, such as in a lyophilised or solubilised state. A particular use of lyophilised fibrinogen of the present invention is within or part of a gauze or bandage (preferably made from polylactic acid compounds used in surgical stitches). Such a wound dressing can be supplied (also incorporating the other components required for the formation of a clot (described above), optionally in a package or kit form, for application direct to the skin or to an internal organ.

Preferred features of the first and fourth aspects of the invention also apply to the fifth aspect.

In the sixth aspect, the present invention provides a method for producing a fibrin adhesive or sealent, comprising mixing fibrinogen with thrombin, wherein the fibrinogen is as set out in the third aspect of the invention.

Factor XIII and $Ca^{2+}$ may also be mixed with the fibrinogen and thrombin.

The method may involve squirting or spraying the components simultaneously or sequentially to the repair site with a syringe or a related device. The mixing may result from two syringes held together along their barrels and at the plungers with the two components mixed either after exiting the needles or in the hub just prior to exiting. Other devices may be used to produce an aerosol or to spray in a variable pattern, depending on the application.

Preferred features of the first, fourth and fifth aspect of the invention also apply to the sixth aspect.

In the seventh aspect, the present invention provides fibrinogen as set out in the third aspect of the invention for use in medicine. Preferably the fibrinogen is used in human medicine. However, it may also be used in veterinary medicine such as for horses, pigs, sheep, cattle, mice and rats as well as domestic pets such as dogs and cats.

While the main use of fibrinogen is thought to be for the preparation of adhesive or sealing agents as described above, fibrinogen has other applications in the field of medicine, for example as a coating for polymeric articles as disclosed in U.S. Pat. No. 5,272,074.

Preferred features of the first aspect of the invention also apply to the seventh aspect.

In the eighth aspect, the present invention also provides a method of surgery or therapy comprising placing on or within an animal or a body part of an animal a seal or an adhesive, comprising fibrinogen as set out in the third aspect of the present invention. Factor XIII, thrombin and $Ca^{2+}$ may also be mixed with the fibrinogen before use. The adhesive or seal may be applied to the repair site by squirting using a syringe or a related device. They may be applied precisely in a very localised site or broadly over a wide area to any biological tissue.

Preferred features of the first, fourth, sixth and seventh aspects of the invention also apply to the eighth aspect.

In the ninth aspect, there is provided the use of fibrinogen for the manufacture of a fibrin adhesive or sealent, wherein the fibrinogen is as set out in the third aspect of the invention.

Preferred features of the first, fourth, sixth, seventh and eighth aspects of the invention also apply to the ninth aspect.

The following examples are given to aid in illustrating the invention, without being limiting.

EXAMPLE 1

Milk from a transgenic ewe expressing human fibrinogen at 5 g/L was thawed from a frozen state and then delipidated using low speed centrifugation (2000 rpm, 15 min) after which the skimmed milk was collected. To this milk was then added a solution of 500 mM ethylene diamine tetracetic acid (EDTA) at pH 8.0 to bring the final EDTA concentration to 100 mM. The pH of the sample was then adjusted to 6.0 by the addition of 25 mM Tris(hydroxymethyl) aminomethane-acetic acid (Tris-acetate) buffer at pH 4.2. Care was used in the addition so that the casein did not precipitate. 0.6 ml of this sample was injected onto a 2.4 ml column of SP-Sepharose™ FF which had been previously equilibrated with 25 mM Tris-acetate buffer, pH 6.0 at a linear flow rate of 88 cm/h. The column was washed with this above solution at the same flow rate until no protein was observed in the effluent as measured by optical density at 280 nm. The column was then irrigated with firstly, 25 mM Tris-acetate buffer at pH 7.5, secondly with 25 mM Tris-acetate buffer at pH 8.5 and lastly with 1M potassium chloride (KCl) in 25 mM Tris acetate at pH 7.7.

The chromatogram from this experiment, shown as FIG. 1, illustrates that a great deal of material did not bind to this column and that material was eluted from the column following irrigation with each of the buffers. The Sodium Dodecyl Sulphate PolyAcrylamide Gel Electrophoresis (SDS-PAGE, 8–16%, Novex) analysis of the experiment shown as FIG. 1b below demonstrates that fibrinogen in the milk (lane 1) was effectively bound by the CEX substrate and was absent in the flow through fraction (lane 2). Non-fibrinogen components, notably casein and β-lactoglobulin that have bound to the column, are effectively removed by changing the pH of the irrigating buffer to 7.5 and 8.5 (lane 3 & 4) while bound fibrinogen is eluted by irrigation of the column with 1M KCl (lane 5). The eluted fibrinogen is of high purity when compared to a commercially available (Enzyme Research Laboratories, UK) plasma derived pure fibrinogen standard (lane 6).

EXAMPLE 2

In another example run under refined conditions it can be demonstrated that removal of non-fibrinogen components from the CEX column can be undertaken using a buffer solution at pH 8.5. This results in a very similar elution pattern to example 1 except that the pH 7.5 elution is not required resulting in an advantage based on processing time. Again the SDS-PAGE demonstrates the selectivity of binding of the fibrinogen to the CEX column as evidenced by its absence in the flow through fraction (Lane 2) when compared to the starting material (Lane 1). Bound fibrinogen can be removed from the column by elution with 0.1M KCl in a buffer at pH 8.5. The high purity of the eluted material (Lanes 5–7) is apparent when examining the purity of a commercially available plasma derived fibrinogen standard (Lane 8).

EXAMPLE 3

Figure 3:
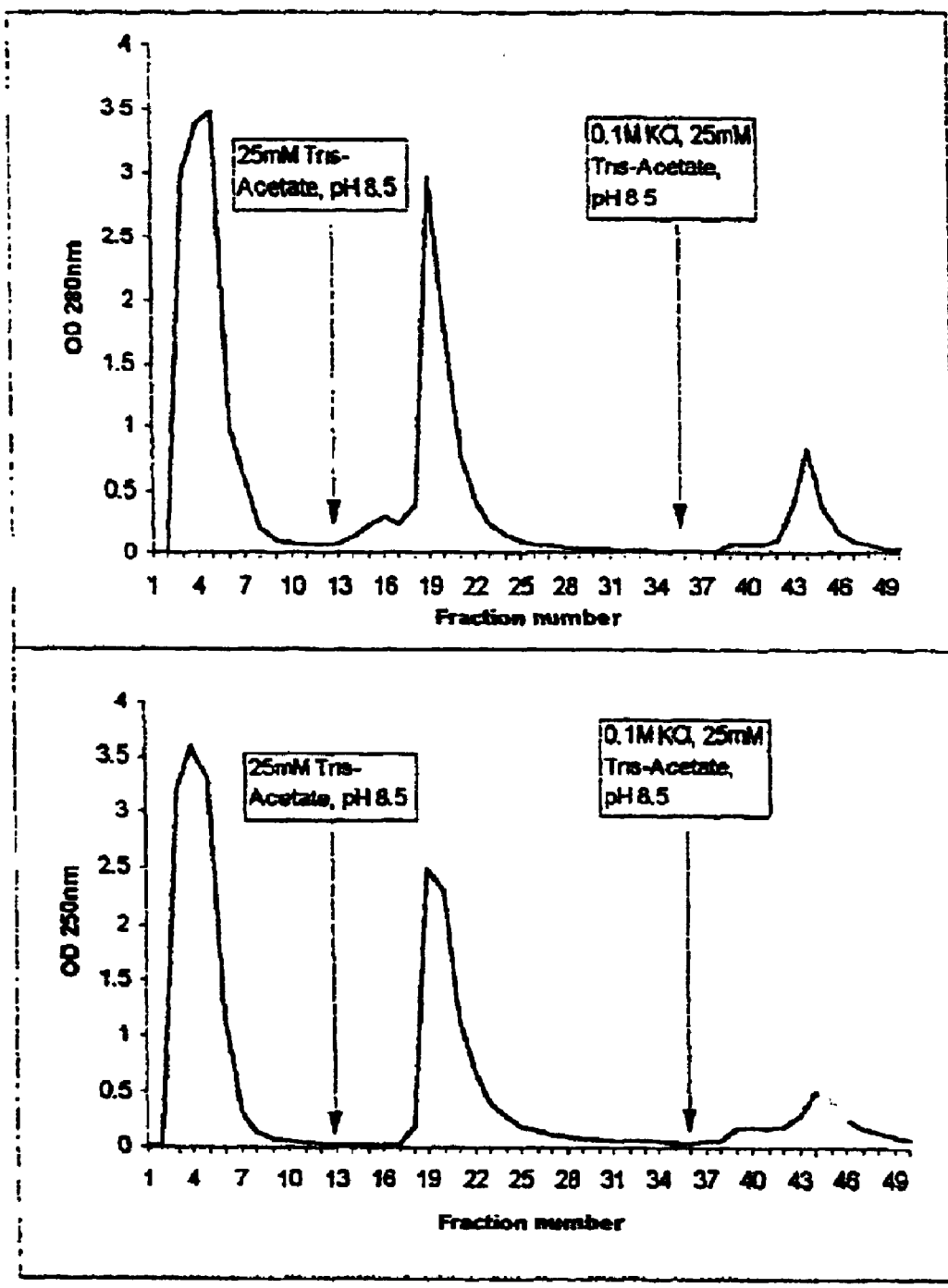
FIG. 3 shows a chromatogram and electrophorogram demonstrating that prior casein resolubilisation is not required in the purification of fibrinogen from milk using CEX.
Figure 3:

In a further example of the applicability of this technique, a procedure, equivalent to example 2 was compared to a procedure where EDTA was not added to the milk. For this application, use was made of SP Sepharose Big Beads. This substrate has a particle size larger than SP Sepharose FF and is better suited for use in particulate containing feedstocks, as it does not exhibit the same occlusion phenomena that is often exhibited by smaller substrate particles. The chromatograms shown in FIG. 3 demonstrate that the resolution obtained by both substrates is remarkably similar. SDS-PAGE analysis (lanes 4 and 9) of the two eluted fibrinogen products confirms the similar high purity obtained from both techniques illustrating that casein resolubilisation or removal is not obligatory for column chromatography.

What is claimed is:

1. A method for obtaining fibrinogen from milk, comprising:
   (a) contacting the milk with a cation exchange chromatography substrate under conditions where the substrate and the milk is at a pH which is higher than the pI of fibrinogen and the fibrinogen binds to the substrate;
   (b) optionally washing the substrate to remove unbound components; and
   (c) removing the bound fibrinogen from the substrate by using irrigating means, which irrigating means has an increased ionic strength or increased pH or both relative to the conditions in step (a).

2. A method as claimed in claim 1 wherein the obtained fibrinogen is at least 60%.

3. A method as claimed in claim 1 wherein the substrate and the milk is at a pH which is greater than pH 5.5.

4. A method as claimed in claim 3 wherein the pH is about pH 6.

5. A method as claimed in claim 1 wherein steps (b) and (c) are performed at a pH greater than pH 5.5 but less than pH 14.0.

6. A method as claimed in claim 5 wherein the washing in step (b) is performed using an irrigating means which has an ionic strength of 0 15M and a pH of 5.5–6.5, or an ionic strength of 0 1 M and a pH of greater than 6.5.

7. A method as claimed in claim 5 wherein the irrigating means in step (c) has an ionic strength of equal to or greater than 0.10 M and a pH of 5.5–6.5, or an ionic strength of equal to or greater than 0.05M and a pH of greater than 6.5.

8. A method as claimed in claim 1 wherein the milk is whole milk, skimmed milk, milk whey or milk fraction.

9. A method as claimed in claim 1 wherein the milk contains one or more agents capable of disrupting casein micelles.

10. A method as claimed in claim 9 wherein the agent is a chelating agent.

11. A method as claimed in claim 9 wherein the agent is EDTA, EGTA or citrate.

12. A method as claimed in claim 1 wherein the substrate is in a batch format or a column format.

13. A method as claimed in claim 12 wherein the column mode of contacting is by fixed bed adsorption, expanded bed adsorption or fluidised bed adsorption.

14. A method as claimed in claim 1 wherein the fibrinogen is transgenic fibrinogen.

15. A method as claimed in claim 1 wherein the fibrinogen is human fibrinogen.

* * * * *